(12) United States Patent
Wada et al.

(10) Patent No.: US 8,523,356 B2
(45) Date of Patent: Sep. 3, 2013

(54) FUNDUS CAMERA

(75) Inventors: Manabu Wada, Kawasaki (JP);
Shigeaki Ono, Tokyo (JP); Shinya Tanaka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 369 days.

(21) Appl. No.: 12/712,084

(22) Filed: Feb. 24, 2010

(65) Prior Publication Data

US 2010/0214535 A1    Aug. 26, 2010

(30) Foreign Application Priority Data

Feb. 26, 2009  (JP) .................................. 2009-043989

(51) Int. Cl.
*A61B 3/14* (2006.01)
*A61B 3/10* (2006.01)

(52) U.S. Cl.
USPC ............................. 351/206; 351/205; 351/221

(58) Field of Classification Search
USPC ........... 351/205–208, 211, 214, 221; 396/18, 396/51, 106; 606/4; 600/558
See application file for complete search history.

(56) References Cited

U.S. PATENT DOCUMENTS

2007/0019160 A1    1/2007  Kleen
2008/0137331 A1*   6/2008  Kaneko et al. ................. 362/231
2008/0191231 A1*   8/2008  Park et al. ........................ 257/98

FOREIGN PATENT DOCUMENTS

JP    2006-174984 A    7/2006
JP    2007-29726 A     2/2007

OTHER PUBLICATIONS

U.S. Appl. No. 12/704,415, filed Feb. 11, 2010.

* cited by examiner

*Primary Examiner* — Mahidere Sahle
(74) *Attorney, Agent, or Firm* — Carter, DeLuca, Farrell & Schmidt LLP

(57) ABSTRACT

A fundus camera includes an irradiation unit including a plurality of LED elements and a fluorescent material that emits light by being excited by light emitted from the LED elements and configured to emit light that is generated by combining light emitted from the LED elements and excitation light from the fluorescent material, an illumination optical system configured to irradiate an eye fundus of a subject's eye with the light emitted by the illumination unit, an observation unit configured to form an eye fundus image by receiving light, which is emitted from the illumination unit and reflected from the eye fundus, and an imaging unit configured to pick up the eye fundus image formed by the observation unit.

18 Claims, 8 Drawing Sheets

FUNDUS CAMERA

BACKGROUND OF THE INVENTION

1. Field of the Invention

The present invention relates to a fundus camera provided with a light-emitting diode (LED) as a light source to illuminate a fundus of a subject's eye.

2. Description of the Related Art

A halogen lamp that emits a fixed light as an observation light source has been used as a light source of a fundus camera and a xenon tube that emits a pulsed light has been used as a photographing light source. In recent years, with higher intensity of white LEDs, lighting apparatuses using, instead of a fluorescent lamp or an incandescent lamp, a white LED with a low heating value and less power consumption as a light source are increasingly used.

Also in the field of the fundus camera, a fundus camera using a white LED as an illumination light source is proposed. A fundus camera discussed in Japanese Patent Application Laid-Open No. 2007-29726 uses a plurality of white LEDs arranged in a ring shape as an illumination light source. LEDs having a plurality of different wavelengths are used, which include at least one LED including white, green, blue, and infrared, and further using at least one LED as a flash light source.

According to Japanese Patent Application Laid-Open No. 2006-174984, a luminous flux is emitted from a plurality of white LEDs arranged in a ring shape as an illumination light source of a fundus camera toward a concave-shaped diffusion reflector and a diffuse-reflected luminous flux is extracted from a ring-shaped opening to generate a uniform illumination light. The plurality of LEDs include a plurality of luminescent colors and further include a white LED and an infrared LED, which are switched alternately according to a photographing mode.

According to Japanese Patent Application Laid-Open No. 2007-29726, when the plurality of white LEDs are arranged in a ring shape, it is difficult to arrange the LEDs without gapping and it is also difficult to form a uniform illumination light, so that an obtained eye fundus image is not uniform in illumination.

According to Japanese Patent Application Laid-Open No. 2006-174984, a concave-shaped diffusion reflector is needed to form a uniform illumination light and thus, a problem that the illumination light source becomes more complex, larger, and more expensive occurs. Further, there is a problem that a luminous flux is diffuse-reflected by a diffusion reflector, thereby causing a loss of quantity of light.

SUMMARY OF THE INVENTION

The present invention is directed to a fundus camera that is small and efficient in emitting light and that can illuminate a fundus uniformly.

According to an aspect of the present invention, a fundus camera includes an irradiation unit including a plurality of LED elements and a fluorescent material that emits light by being excited by light emitted from the LED elements and configured to emit light that is generated by combining light emitted from the LED elements and excitation light from the fluorescent material, an illumination optical system configured to irradiate an eye fundus of a subject's eye with the light emitted by the illumination unit, an observation unit configured to form an eye fundus image by receiving light, which is emitted from the illumination unit and reflected from the eye fundus, and an imaging unit configured to pick up the eye fundus image formed by the observation unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
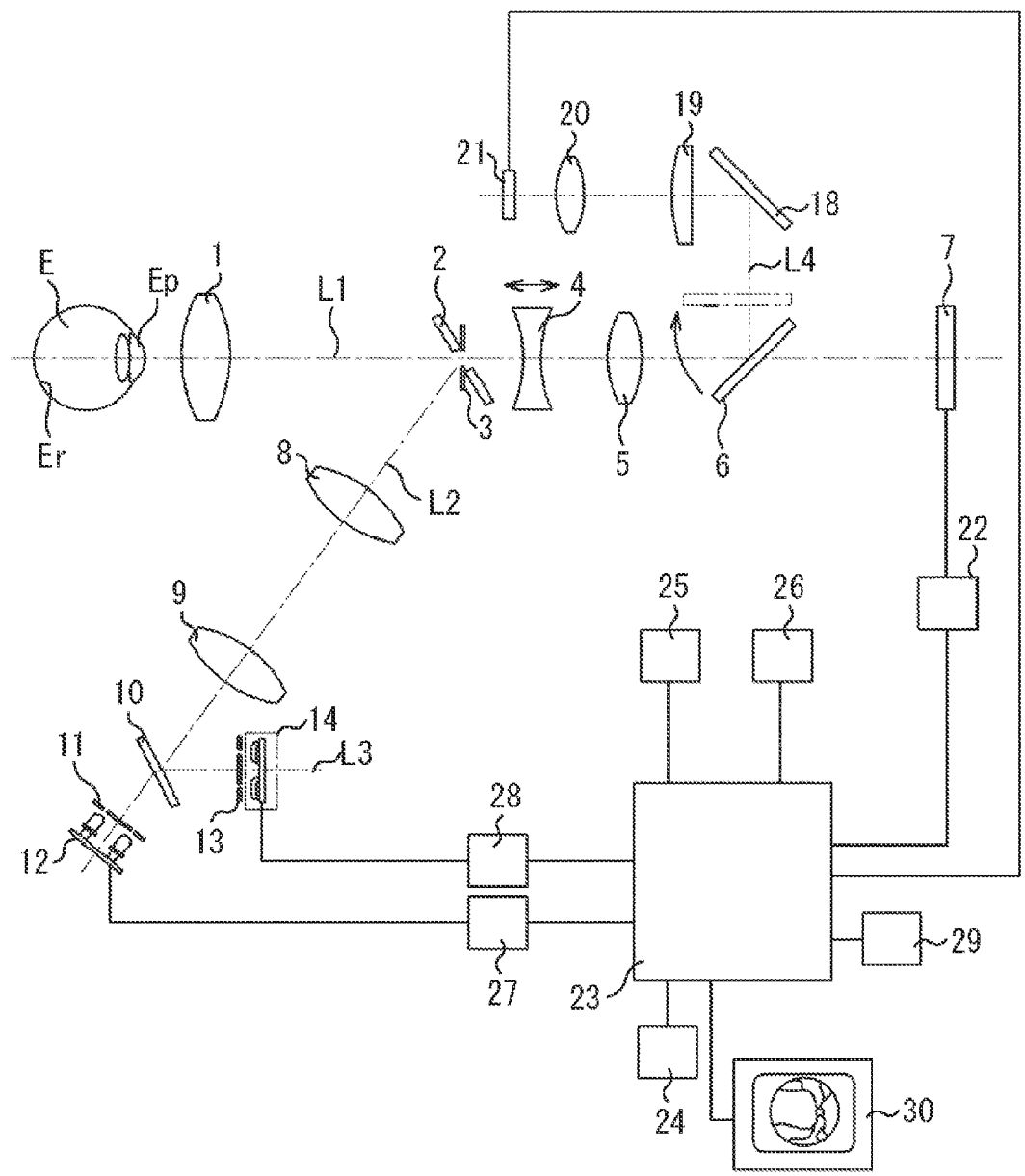
FIG. 1 illustrates a configuration of a fundus camera according to a first exemplary embodiment.

FIG. 1 illustrates a configuration of a non-mydriatic fundus camera according to a first exemplary embodiment. An objective lens 1, a perforated mirror 2, an photographing diaphragm 3, a focusing lens 4 movable in an optical axis, an imaging lens 5, a bouncing mirror 6, and an image sensor 7 that mainly picks up still images and has sensitivity to visible light are successively arranged on an optical axis L1 in front of an eye E to be examined to configure an eye fundus imaging optical system.

On an optical axis L2 in an incidence direction of the perforated mirror 2, relay lenses 8 and 9, a dichroic mirror 10 that transmits infrared light and reflects visible light, a ring diaphragm 11 having a ring-shaped opening, and an observation illumination light source 12 including infrared LEDs are arranged. The ring diaphragm 11 is arranged at a position optically conjugate to a pupil Ep of the eye E to be examined via the objective lens 1 and the relay lenses 8 and 9 to configure an eye fundus observation illumination optical system.

On an optical axis L3 in the incidence direction of the dichroic lens 10, a ring diaphragm 13 serving as a luminous flux limiting unit and a photographing illumination light source 14 serving as an illumination unit that irradiates a neighborhood of the position conjugate to an anterior eye segment of the eye E to be examined with visible light to configure an eye fundus photographing illumination optical system. The ring diaphragm 13 is arranged at a position optically conjugate to the pupil Ep of the eye E to be examined.

Figure 2A:
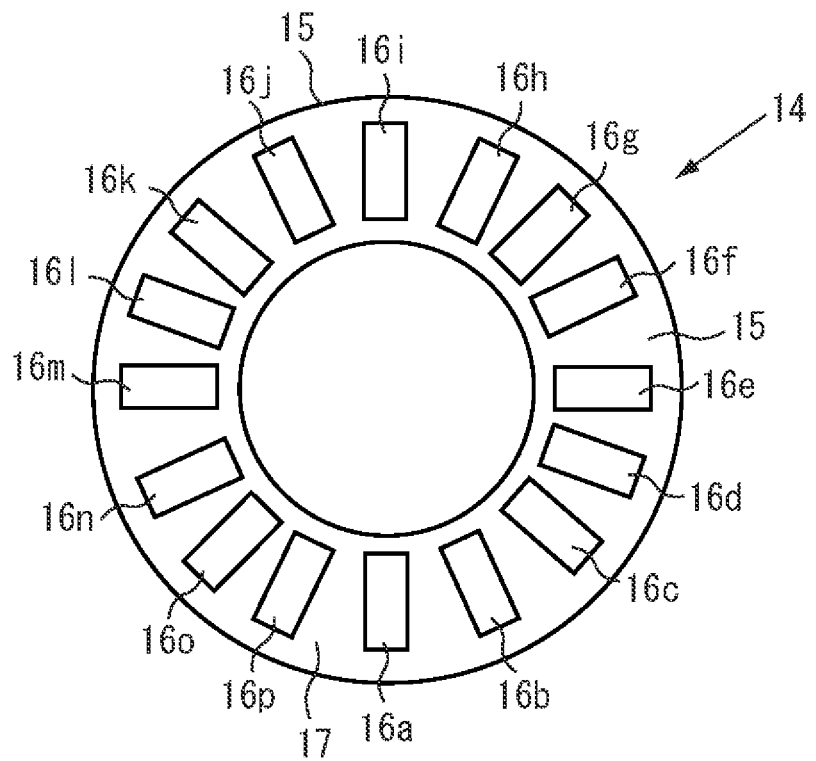
FIGS. 2A and 2B are a front view and a sectional view of a photographing illumination light source, respectively.
Figure 2B:
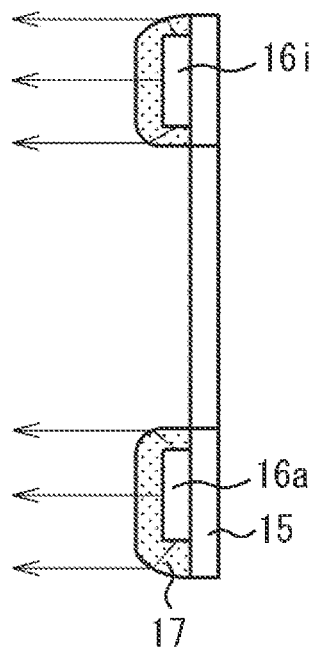

FIG. 2A is a front view of the photographing illumination light source 14 when viewed from the side of the ring diaphragm 13 and FIG. 2B is a sectional view thereof. In the photographing illumination light source 14, for example, 16 blue LED elements 16a to 16p that emit blue light onto a substrate 15 are arranged discretely in a ring shape. Spaces among the blue LED elements 16a to 16p arranged discretely in a ring shape are filled with a fluorescent material 17 without gapping and also the surface of the blue LED elements 16a to 16p is covered with the fluorescent material 17.

On an optical axis L4 in a reflection direction of the bouncing mirror 6, a mirror 18, a field lens 19, a television relay lens 20, and an image sensor 21 including a CCD camera mainly for moving image observation are arranged to configure an eye fundus image observation optical system.

The above-described eye fundus imaging optical system, eye fundus observation illumination optical system, eye fundus photographing illumination optical system, and eye fundus image observation optical system are contained inside a camera casing to configure an eye fundus camera optical unit. The eye fundus camera optical unit is placed on a slide base to enable alignment with the subject's eye E.

An output from the image sensor 7 is converted into a digital signal through an A/D conversion unit 22, which is connected to a control unit 23 such as a central processing unit (CPU) that controls the whole apparatus. Moreover, an output from the image sensor 21 and an output from a character generator 24 that generates a character for combining information (e.g., a light quantity set value necessary for observation or photographing and an alignment reference position) with a video signal of the image sensor 21 are connected to the control unit 23. Further, outputs of an operation unit 25 that is used to set photographing conditions such as an observation light quantity and photographing light quantity, and a photographing switch 26 are connected to the control unit 23.

An output from the control unit 23 is connected to an observation light quantity control unit 27 for controlling the observation illumination light source 12 and a photographing light quantity control unit 28 for controlling the photographing illumination light source 14 and further, a memory 29 that stores eye fundus images and a monitor 30 are connected to the control unit 23.

When the observation light quantity is set through the operation unit 25, the observation light quantity control unit 27 controls the current for driving the observation illumination light source 12 according to the set value. Similarly, when the photographing light quantity is set through the operation unit 25, the photographing light quantity control unit 28 controls the current for driving the photographing illumination light source 14 according to the set value.

Infrared light emitted from the observation illumination light source 12 passes through the dichroic mirror 10 after a luminous flux thereof being limited by the ring diaphragm 11 and passes through the relay lenses 9 and 8 to form an image of the ring diaphragm 11 on the perforated mirror 2, and then reflected in the direction of the objective lens 1. Then, the image of the ring diaphragm 11 is re-formed near the pupil Ep of the subject's eye E by the objective lens 1 to illuminate a fundus Er of the subject's eye.

A luminous flux reflected/scattered by the fundus Er illuminated by the eye fundus observation illumination optical system goes out from the subject's eye E at a region inside the image of the ring diaphragm 11 by the illuminating luminous flux of the pupil Ep to enter the bouncing mirror 6 via the objective lens 1, the photographing diaphragm 3, the focusing lens 4, and the imaging lens 5.

Then, the luminous flux is reflected by the bouncing mirror 6 and the mirror 18 to form an image of the eye fundus Er near the field lens 19 and is received and imaged by the image sensor 21 via the television relay lens 20 and an eye fundus image is displayed on the monitor 30.

An operator sets the quantity of light of the observation illumination light source 12 through the operation unit 25 so that the eye fundus image in the monitor 30 has appropriate brightness and uses a console (not illustrated) to align the subject's eye E and the eye fundus camera optical unit. Further, the operator moves the focusing lens 4 in the optical axis direction by operating a focus knob (not illustrated) to bring the eye fundus image on the monitor 30 into focus.

When the operator presses the photographing switch 26 after positioning and focusing are completed, the control unit 23 causes the bouncing mirror 6 to bounce to the position indicated by a dotted line in FIG. 1 and controls the photographing light quantity control unit 28 to cause the photographing illumination light source 14 to emit pulsed light.

Figure 3:
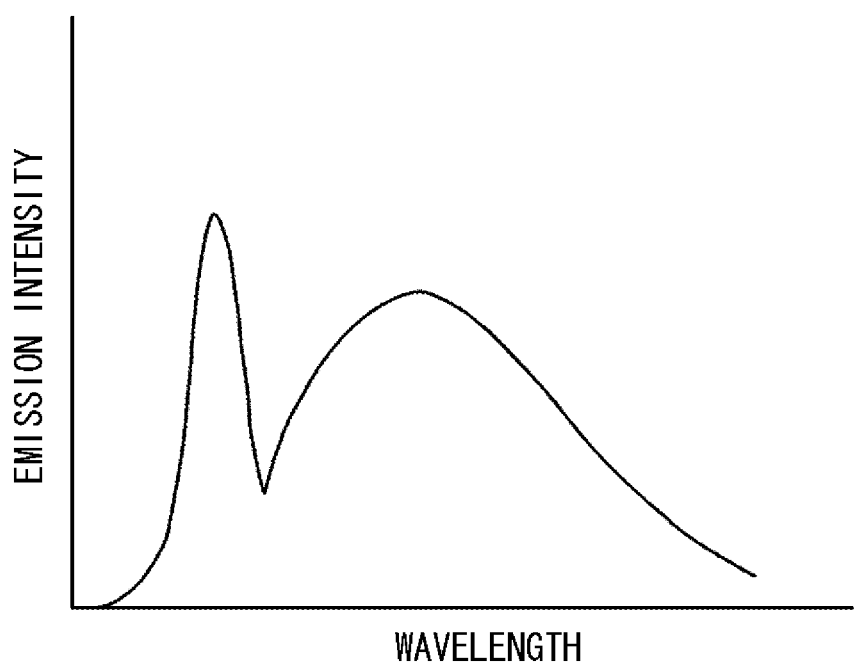
FIG. 3 is a graph of an emission spectrum of the photographing illumination light source.

In other words, the blue light emitted from the blue LED elements 16a to 16p of the photographing illumination light source 14 excites the fluorescent material 17 to generate fluorescence. Then, white light is formed by mixing fluorescence excited from the fluorescent material 17 and blue light directly emitted without exciting the fluorescent material 17, and an emission spectrum thereof is, as illustrated in FIG. 3, light of wavelength bands containing up to red, which is the excitation light wavelength.

In other words, as illustrated in FIGS. 2A and 2B, the blue light emitted from the front surface of the blue LED elements 16a to 16p and fluorescence excited by the fluorescent material 17 covering the front surface are combined to generate white light. The blue light emitted from the side surface of the blue LED elements 16a to 16p also excites the fluorescent material 17 to generate fluorescence, which is combined with the blue light to generate white light.

In the present exemplary embodiment, space among the blue LED elements 16a to 16p is filled with the fluorescent material 17 without gapping and thus, light emitted from the side surface of the blue LED elements 16a to 16p can also be used. With the generated white light, uniform illumination light can be obtained and also light can be used more efficiently.

The photographing illumination light source 14 is provided with a heat dissipation unit (not illustrated) on the rear side of the substrate 15, which is the opposite side of the emission direction, to prevent life degradation caused by heat.

The white light emitted from the photographing illumination light source 14 is reflected by the dichroic mirror 10 in the direction of the relay lens 9 after a luminous flux thereof is limited by the ring diaphragm 13. Then, like the observation illumination light, the white light illuminates the fundus Er of the subject's eye E.

The light reflected from the fundus Er goes out from the subject's eye E at a region inside the image of the ring diaphragm 11 by the illuminating luminous flux of the pupil Ep to enter the image sensor 7 via the objective lens 1, the photographing diaphragm 3, the focusing lens 4, and the imaging lens 5 for imaging. An eye fundus image picked up by the image sensor 7 is input into the control unit 23 via the A/D conversion unit 22, stored in the memory 29, and also displayed on the monitor 30.

The photographing illumination light source 14 in the first exemplary embodiment has a simple configuration and thus, the illumination light source can be made inexpensive and small. While the photographing illumination light source 14 has the 16 blue LED elements 16a to 16p that emit blue light in the first exemplary embodiment, for example, purple or ultraviolet-blue LED elements that emit light of a wavelength shorter than that of blue may also be used.

Figure 4A:
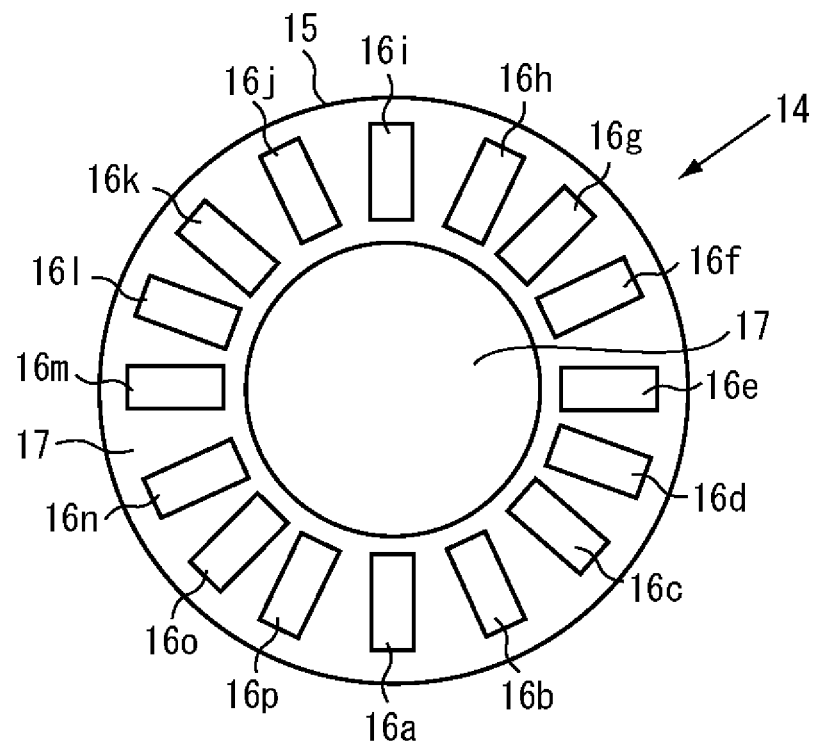
FIGS. 4A and 4B are a front view and a sectional view of a modification example of the photographing illumination light source according to the first exemplary embodiment.
Figure 4B:
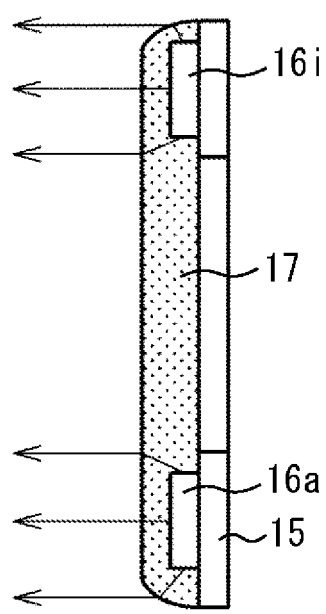

Moreover, the first exemplary embodiment is described by taking a case where the fluorescent material 17 is formed in a ring shape as an example, but any shape, in which a plurality of the blue LED elements 16a to 16p are arranged discretely in a ring shape and covered with the fluorescent material 17, may also be adopted. For example, a circular region in the center illustrated in FIGS. 4A and 4B may also be filled with the fluorescent material 17.

Figure 5:
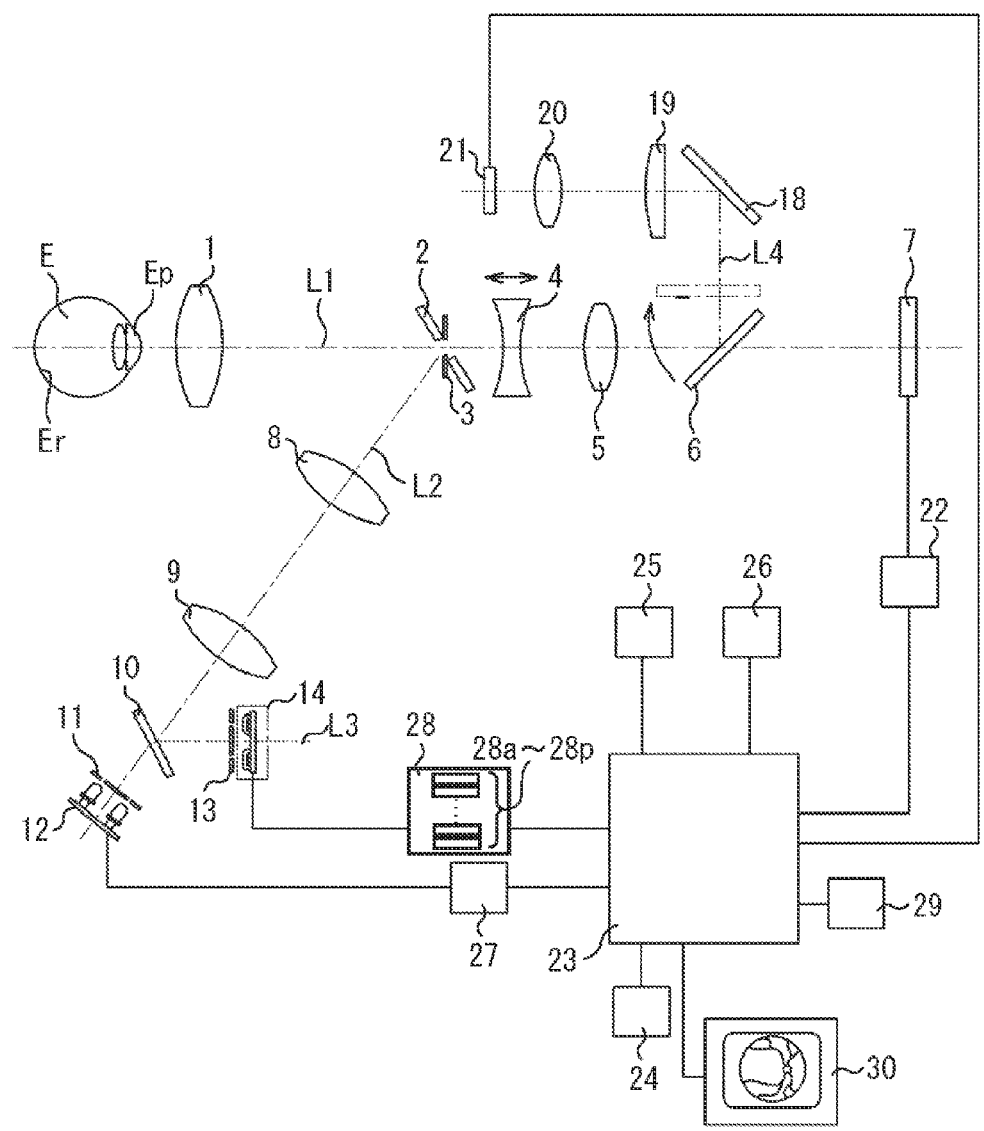
FIG. 5 illustrates a configuration of the fundus camera according to a second exemplary embodiment.

FIG. 5 illustrates a configuration of a non-mydriatic fundus camera according to a second exemplary embodiment. The same reference numerals are denoted to the similar members to those described in the first exemplary embodiment. In the second exemplary embodiment, the photographing light quantity control unit 28 is provided with constant current circuits 28a to 28p.

Figure 6:
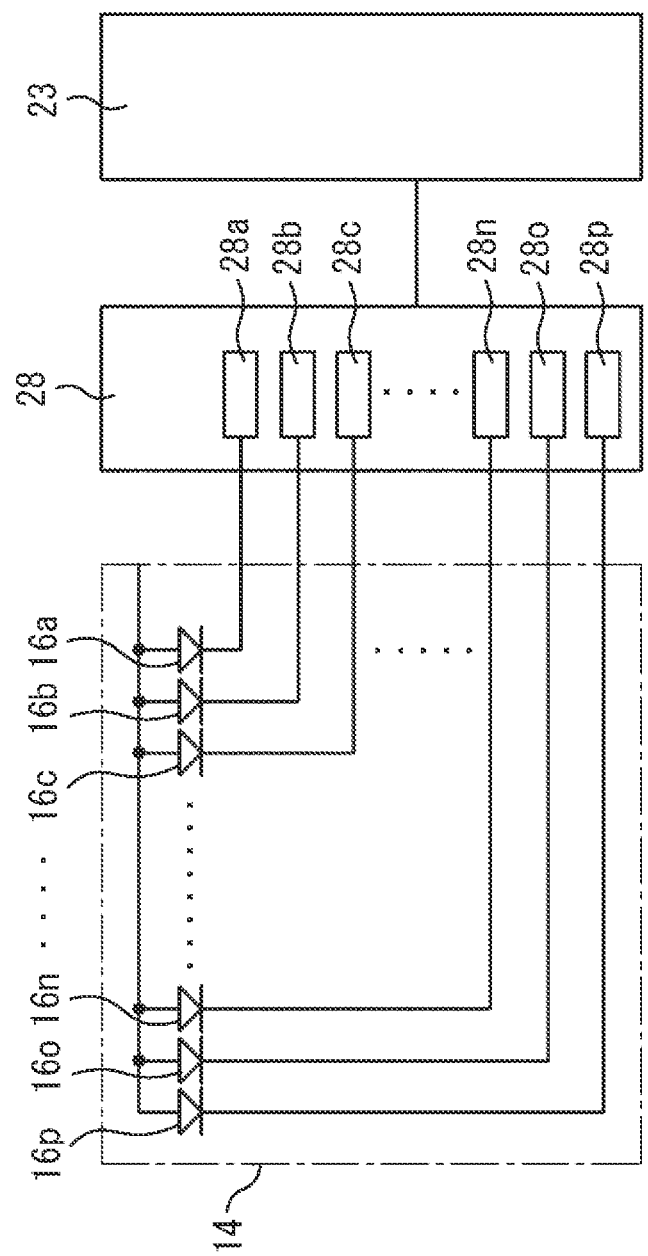
FIG. 6 is a block diagram illustrating a circuit configuration.

FIG. 6 is a block diagram illustrating a circuit configuration including the photographing illumination light source 14, the control unit 23, the photographing light quantity control unit 28, and the constant current circuits 28 a to 28p. The photographing light quantity control unit 28 is provided with the as many constant current circuits 28 a to 28 p as the blue LED elements 16a to 16p of the photographing illumination light source 14.

The constant current circuits 28 a to 28 p are connected to the corresponding blue LED elements 16a to 16p respectively to control the current that flow through the blue LED elements 16a to 16p independently.

In general, even if the same current is applied to the blue LED elements 16a to 16p, the emission amounts are different due to structural fluctuations. To correct such fluctuations in emission amount, if, for example, brightness of the blue LED element 16a is darker than that of the blue LED element 16b, the constant current circuit 28 a increases the current that is applied to the blue LED element 16a so that a larger amount of current is applied to the blue LED element 16a than that to the blue LED element 16b. Accordingly, the blue LED elements 16a and 16b can be controlled to emit equal amounts of blue light.

On the other hand, when brightness of the blue LED element 16a is brighter than that of the blue LED element 16b, the constant current circuit 28 a decreases the current that is applied to the blue LED element 16a so that a smaller amount of current is applied to the blue LED element 16a than that to the blue LED element 16b. Accordingly, the blue LED elements 16a and 16b can emit an equal amount of light.

Thus, a more uniform illumination light source can be realized by using the constant current circuits 28 a to 28p and controlling the current that is applied to the blue LED elements 16a to 16p independently to cause all the blue LED elements 16a to 16p to emit an equal amount of light.

Figure 7:
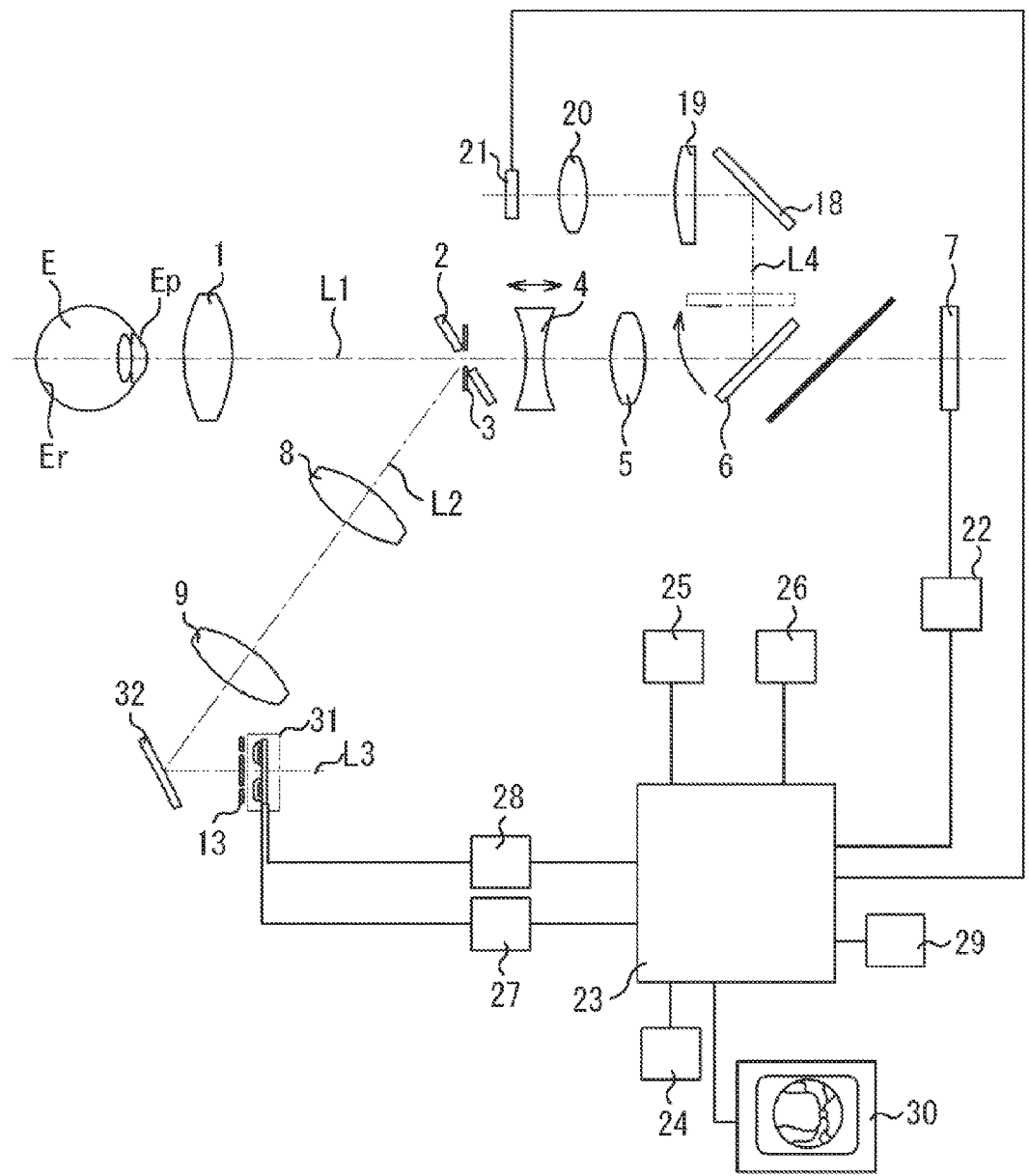
FIG. 7 illustrates a configuration of the fundus camera according to a third exemplary embodiment.

FIG. 7 illustrates a configuration of a non-mydriatic fundus camera according to a third exemplary embodiment and the same reference numerals are denoted to the similar members to those in the first exemplary embodiment. In the third exemplary embodiment, instead of the observation illumination light source 12 and the photographing illumination light source 14 in the first exemplary embodiment, one illumination light source 31 is used.

Accordingly, the ring diaphragm 11 in the first exemplary embodiment is not needed and further, while the dichroic mirror 10 is used in the first exemplary embodiment, a total reflection mirror 32 that reflects both visible light and infrared light can be used in the third exemplary embodiment.

Moreover, an output from the control unit 23 is connected to the illumination light source 31 via the observation light quantity control unit 27 and the photographing light quantity control unit 28.

Figure 8:
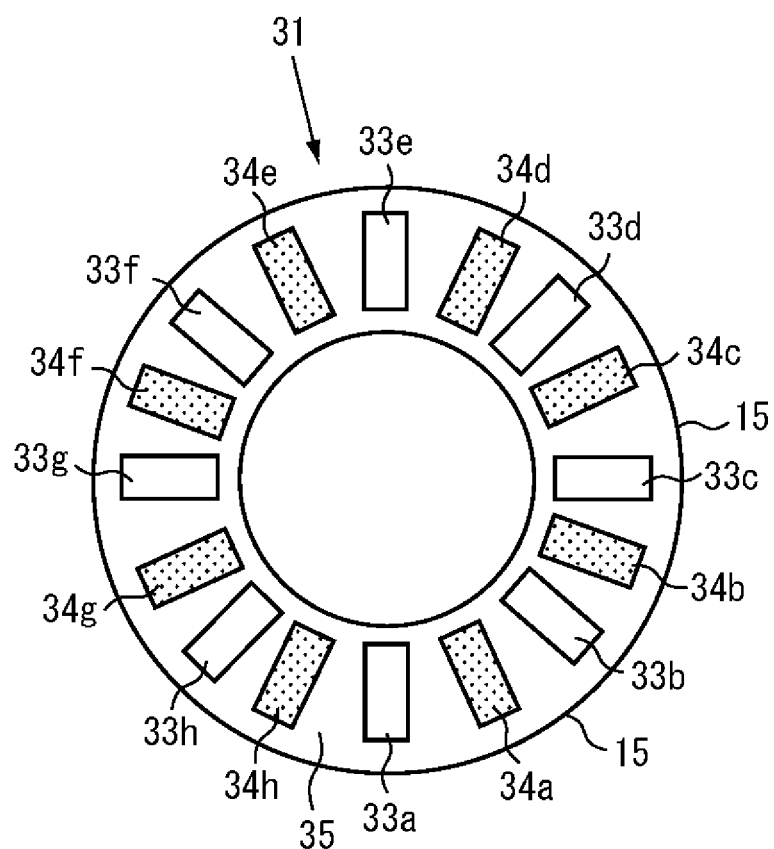
FIG. 8 is a front view of the photographing illumination light source.

FIG. 8 illustrates a front view when the illumination light source 31 is viewed from the side of the ring diaphragm 13. The illumination light source 31 has a plurality of blue LED elements 33a to 33h that emit blue light, and a plurality of infrared LED elements 34a to 34h that emit near-infrared light arranged discretely in a ring shape on an upper surface of the substrate 15.

Spaces among the blue LED elements 33a to 33h and the infrared LED elements 34a to 34h are filled with a fluorescent material 35 without gapping and also the surfaces of the blue LED elements 33a to 33h and the infrared LED elements 34a to 34h are covered with the fluorescent material 35.

The fluorescent material 35 emits fluorescence excited by blue light emitted from the blue LED elements 33a to 33h to generate white light by combination with the blue light, and transmits near-infrared light unchanged.

It is desirable to arrange, as illustrated in FIG. 8, the blue LED elements 33a to 33h and the infrared LED elements 34a to 34h alternately to obtain uniform illumination light.

Infrared light emitted from the infrared LED elements 34a to 34h of the illumination light source 31 passes through the fluorescent material 35 and is reflected by the total reflection mirror 32 after a luminous flux thereof is limited by the ring diaphragm 13 to form an image of the ring diaphragm 13 on the perforated mirror 2 via the relay lenses 9 and 8.

Then, the infrared light is reflected by the perforated mirror 2 in the direction of the objective lens 1 to re-form the image of the ring diaphragm 13 near the pupil Ep of the subject's eye E by the objective lens 1 to illuminate the fundus Er of the subject's eye E.

The infrared light, which is emitted from the illumination light source 31 by the eye fundus observation illumination unit and reflected/scattered by the eye fundus Er, is received and imaged by the image sensor 21 after passing through the same light path as that described in the first exemplary embodiment, and an eye fundus image is displayed on the monitor 30 after being input into the control unit 23.

The operator sets amounts of light of the infrared LED elements 34a to 34h through the operation unit 25 so that the eye fundus image displayed on the monitor 30 has appropriate brightness, and aligns the subject's eye E and the eye fundus camera optical unit using a console.

Further, the operator moves the focusing lens 4 in the optical axis direction by operating a focus knob to bring the displayed eye fundus image into focus.

The operator presses the photographing switch 26 after positioning and focusing are completed. Accordingly, the control unit 23 causes the bouncing mirror 6 to bounce to the position of a dotted line and controls the observation light quantity control unit 27 to turn off the infrared LED elements 34a to 34h of the illumination light source 31.

Subsequently, the control unit 23 controls the photographing light quantity control unit 28 to cause the blue LED elements 33a to 33h of the illumination light source 31 to emit pulsed light. While light is formed by combining blue light from the blue LED elements 33a to 33h with fluorescence from the fluorescent material 35.

The white light emitted from the illumination light source 31 is reflected by the total reflection mirror 32 after a luminous flux thereof is limited by the ring diaphragm 13 to illuminate the eye fundus Er after passing through the similar light path to that in the first and second exemplary embodiments.

The light reflected/scattered by the eye fundus Er enters the image sensor 7 and an eye fundus image is input into the control unit 23 via the A/D conversion unit 22 to be stored in the memory 29 and also to be displayed on the monitor 30.

In the third exemplary embodiment, spaces among the blue LED elements 33a to 33h and the infrared LED elements 34a to 34h are filled with the fluorescent material 35 without gapping and thus, the combined white light illuminates the eye fundus Er uniformly and illumination light with high utilization efficiency of light is obtained.

The illumination light source 31 in the third exemplary embodiment uses the eight blue LED elements 33a to 33h that emit blue light, however, for example, purple or ultraviolet-blue LED elements that emit light of a shorter wavelength may also be used.

While the first to third exemplary embodiments are described by taking a non-mydriatic fundus camera as an example, the present invention may also be applied to a mydriatic fundus camera.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2009-043989 filed Feb. 26, 2009, which is hereby incorporated by reference herein in its entirety.

What is claimed is:

1. A fundus camera comprising:
   an illumination unit including a plurality of LED elements each emitting nearly blue light and a fluorescent material that is excited by light emitted from the plurality of LED elements and configured to illuminate a subject's eye with excitation light from the fluorescent material; and
   an imaging unit configured to take a fundus image of the subject's eye based on light reflected from the subject's eye,
   wherein a front surface and a side surface of the plurality of LED elements are covered with the fluorescent material, and
   wherein spaces among the plurality of LED elements are filled with the fluorescent material.

2. The fundus camera according to claim 1, wherein the illumination unit includes the plurality of LED elements arranged in a ring shape and the illumination unit illuminates the subject's eye with the light that is generated by combining light emitted from the plurality of LED elements and the excitation light.

3. The fundus camera according to claim 1, wherein the plurality of LED elements emit, as the nearly blue light, at least one of blue light and light having a wavelength that is shorter than that of the blue light.

4. The fundus camera according to claim 1, wherein the fluorescent material generates light having an emission spectrum containing up to red of an excitation light wavelength.

5. The fundus camera according to claim 1, wherein the illumination unit includes a heat dissipation unit for dissipating heat on an opposite side of an emission direction.

6. The fundus camera according to claim 1, further comprising a light quantity control unit configured to independently control a quantity of light of each LED element.

7. The fundus camera according to claim 1, wherein the plurality of LED elements are blue LED elements, a plurality of infrared LEDs are provided among the plurality of blue LED elements, and the fluorescent material has a transmittance in near-infrared light.

8. An ophthalmologic photographing apparatus, comprising:
   an illumination unit including a plurality of blue LED elements and a fluorescent material that covers a front surface and a side surface of the plurality of blue LED elements and emits fluorescent light by being excited by light emitted from the plurality of blue LED elements and configured to illuminate a subject's eye with visible light; and
   an imaging unit configured to take an image of the subject's eye based on light reflected from the subject's eye,
   wherein the illumination unit further includes a plurality of infrared LED elements that emit near-infrared light and are provided among the plurality of blue LED elements, and
   wherein the fluorescent material covers the plurality of infrared LED elements.

9. The ophthalmologic photographing apparatus according to claim 8,
   wherein the near-infrared light emitted from the plurality of infrared LED elements illuminates the subject's eye by transmitting through the fluorescent material.

10. An ophthalmologic photographing apparatus, comprising:
    an illumination unit including a plurality of LED elements each emitting nearly blue light and a fluorescent material that covers a front surface and a side surface of the plurality of LED elements, fills spaces among the plurality of LED elements and emits fluorescent light by being excited by light emitted from the plurality of LED elements and configured to illuminate a subject's eye with visible light, and
    an imaging unit configured to take an image of the subject's eye based on light reflected from the subject's eye.

11. The ophthalmologic photographing apparatus according to claim 10, wherein each of the plurality of LED elements emits, as the nearly blue light, at least one of blue light and light having a wavelength that is shorter than that of the blue light.

12. The ophthalmologic photographing apparatus according to claim 10,
    wherein the plurality of LED elements are blue LED elements, and
    wherein the illumination unit further includes a plurality of infrared LED elements that emit near-infrared light and are provided among the plurality of blue LED elements.

13. The ophthalmologic photographing apparatus according to claim 12,
    wherein the fluorescent material covers the plurality of infrared LED elements, and
    wherein the near-infrared light emitted from the plurality of infrared LED elements illuminates the subject's eye by transmitting through the fluorescent material.

14. The ophthalmologic photographing apparatus according to claim 10, wherein the illumination unit includes a heat dissipation unit for dissipating heat on an opposite side of an emission direction.

15. The ophthalmologic photographing apparatus according to claim 10, further comprising a light quantity control unit configured to independently control a quantity of light of each LED element.

16. The ophthalmologic photographing apparatus according to claim 15, wherein the light quantity control unit independently controls the quantity of light of each LED element so as to correct variation in light quantity of each of the plurality of LED elements.

17. The ophthalmologic photographing apparatus according to claim 10, wherein the plurality of LED elements are arranged in an approximate ring shape and disposed separately from each other.

18. An ophthalmologic photographing apparatus comprising:
- an illumination unit including a plurality of LED elements each emitting nearly blue light and a fluorescent material that covers a front surface and a side surface of the plurality of LED elements and emits fluorescent light by being excited by light emitted from the plurality of LED elements and configured to irradiate a subject's eye with visible light; and
- a light quantity control unit configured to independently control a quantity of light of each LED element so as to correct variation in light quantity of each of the plurality of LED elements.

* * * * *